US009125828B2

(12) United States Patent
Behan et al.

(10) Patent No.: US 9,125,828 B2
(45) Date of Patent: Sep. 8, 2015

(54) MOC COMPOSITIONS

(75) Inventors: John Martin Behan, Ashford Kent (GB); Keith Douglas Perring, Ashford Kent (GB); Alan Forbes Provan, Ashford Kent (GB)

(73) Assignee: Givaudan SA, Vernier (CH)

( * ) Notice: Subject to any disclaimer, the term of this patent is extended or adjusted under 35 U.S.C. 154(b) by 267 days.

(21) Appl. No.: 13/988,247

(22) PCT Filed: Dec. 13, 2011

(86) PCT No.: PCT/EP2011/072590
§ 371 (c)(1),
(2), (4) Date: Sep. 3, 2013

(87) PCT Pub. No.: WO2012/080235
PCT Pub. Date: Jun. 21, 2012

(65) Prior Publication Data
US 2013/0336911 A1 Dec. 19, 2013

(30) Foreign Application Priority Data

Dec. 13, 2010 (GB) .................................. 1021050.8

(51) Int. Cl.
| | | |
|---|---|---|
| *A61K 8/30* | (2006.01) | |
| *A61Q 15/00* | (2006.01) | |
| *C11B 9/00* | (2006.01) | |
| *A61K 8/35* | (2006.01) | |
| *A61K 8/37* | (2006.01) | |
| *A61K 8/40* | (2006.01) | |
| *A61K 8/49* | (2006.01) | |
| *A61Q 5/02* | (2006.01) | |
| *A61Q 5/06* | (2006.01) | |
| *A61Q 5/12* | (2006.01) | |
| *A61Q 19/10* | (2006.01) | |

(52) U.S. Cl.
CPC ... *A61K 8/30* (2013.01); *A61K 8/35* (2013.01); *A61K 8/37* (2013.01); *A61K 8/40* (2013.01); *A61K 8/498* (2013.01); *A61K 8/4973* (2013.01); *A61Q 15/00* (2013.01); *C11B 9/003* (2013.01); *C11B 9/008* (2013.01); *C11B 9/0023* (2013.01); *C11B 9/0034* (2013.01); *C11B 9/0038* (2013.01); *C11B 9/0049* (2013.01); *C11B 9/0053* (2013.01); *C11B 9/0057* (2013.01); *C11B 9/0061* (2013.01); *C11B 9/0065* (2013.01); *C11B 9/0076* (2013.01); *C11B 9/0084* (2013.01); *C11B 9/0092* (2013.01); *A61Q 5/02* (2013.01); *A61Q 5/06* (2013.01); *A61Q 5/12* (2013.01); *A61Q 19/10* (2013.01)

(58) Field of Classification Search
CPC ........... A61K 8/37; A61K 8/40; A61K 8/498; A61K 8/585; A61Q 15/00
See application file for complete search history.

(56) References Cited

U.S. PATENT DOCUMENTS

| 6,069,125 A | 5/2000 | Pesaro |
| 2004/0248762 A1 | 12/2004 | McGee et al. |

FOREIGN PATENT DOCUMENTS

| EP | 1884555 A2 | 2/2008 | |
| WO | 2006133592 A1 | 12/2006 | |
| WO | WO2006/133592 A1 * | 12/2006 | ..................... 424/401 |

(Continued)

OTHER PUBLICATIONS

Notification of Transmittal of the International Search Report and the Written Opinion of the International Searching Authority for PCT/EP2011/072590 dated Mar. 23, 2012.

(Continued)

*Primary Examiner* — Andrea Buckley
(74) *Attorney, Agent, or Firm* — Norris McLaughlin & Marcus PA

(57) ABSTRACT

A Malodour counteracting composition, in particular a deodorant composition, comprising at least 25% w/w in total of at least 3 compounds drawn from Group A and Group B following:
A. at least 5% in total of at least one of the following compounds: 2-Cyclohexylidene-2-phenylacetonitrile, 2-Acetyl-1,2,3,4,5,6,7,8-octahydro-1,2,8,8-tetramethylnapthalene, cyclohexylidene(2-methylphenyl)acetonitrile, 2-Ethoxy-4-formylphenyl (E)-3-(2-hydroxyphenyl)acrylate and (E)-Dec-9-enyl 3-(2-hydroxyphenyl) acrylate.
B. optionally, at least one of the following compounds: 3,8,8,11a-Tetramethyldodecahydro-5H-3,5a-epoxynapth[2,1-C]oxepin, Oxacycloheptadec-10-en-2-one, 3-Methyl-5-(2,2,3-trimethyl-3-cyclopenten-1-yl)-4-penten-2-ol, Ethyl 2,6,6-trimethyl-1,3-cyclohexadiene-1-carboxylate, 2-Methyl-3-(4-methoxyphenyl)propanal, 3-(3-isopropylphenyl)butanal, 2(6)-Methyl-8-(1-methylethyl)bicyclo[2.2.2]oct-5-en-2(3)-yl-1,3-dioxolane, 1-Methyl-2-(1,2,2-trimethylbicyclo[3.1.0]-hex-3-ylmethyl)cyclopropyl)methanol, 3,7-Dimethyl-2(3),6-nonadienonitrile, 2-(2-(4-Methyl-3-cyclohexen-1-yl)propyl)cyclopentanone, 2-Cyclohexyl-1,6-heptadien-3-one, (2Z)-2-ethyl-4-(2,2,3-trimethylcyclopent-3-en-1-yl)but-2-en-1-ol, 2-{[1-(3,3-dimethylcyclohexyl)ethyl]oxy}-2-methylpropyl cyclopropanecarboxylate, 1-Spiro[4.5]dec-7-en-7-yl-4-penten-1-one, 1-spiro[4.5]dec-6-en-7-yl-4-penten-1-one, 1-(trimethylcyclododecatrienyl)-Ethanone, 4-cyclooocten-1-ylmethyl carbonate, 2-(2,4-dimethylcyclohexyl)-pyridine,
wherein the calculation of the weight percentage of every component has been performed on the basis that the presence of any diluent is ignored. The use of said composition to counteract malodour, and in malodour counteracting products.

13 Claims, No Drawings

(56) References Cited

FOREIGN PATENT DOCUMENTS

| | | |
|---|---|---|
| WO | 2007030961 A2 | 3/2007 |
| WO | 2008055372 A1 | 5/2008 |
| WO | 2008104352 A2 | 9/2008 |
| WO | 2009052643 A1 | 4/2009 |

OTHER PUBLICATIONS

International Search Report for PCT/EP2011/072590 dated Mar. 23, 2012.
Written Opinion of the International Searching Authority for PCT/EP2011/072590 dated Mar. 23, 2012.
GB Search Report for application GB1021050.8 dated Mar. 10, 2011.

* cited by examiner

MOC COMPOSITIONS

This is an application filed under 35 USC 371 of PCT/EP2011/072590.

FIELD OF THE INVENTION

This invention relates to the combined use of certain fragrance compounds to counteract malodour, in particular body malodour, to malodour counteracting compositions and products, in particular deodorant and antiperspirant products, and to a method of counteracting malodour.

BACKGROUND TO THE INVENTION

Malodours are offensive odors which may be personal and/or environmental in origin. They may be encountered in the air and/or on many surfaces such as fabrics, hard surfaces, skin, and hair.

Industry is constantly looking for compounds, or combinations thereof, possessing malodour, in particular body malodour, counteracting (MOC) properties. Such compounds may be used in MOC products such as deodorants and antiperspirants.

Many fragrance compounds, and compositions thereof, are known to possess MOC properties. However, there is an on going need for the identification of fragrance compounds, or combinations thereof, possessing superior malodour, in particular body malodour, counteracting properties. Such fragrance compounds, or combinations thereof, may positively impact both the MOC and hedonic properties of compositions and/or products to which they are added, resulting in increased consumer acceptance.

DETAILED DESCRIPTION

It has now been found that certain known fragrance compounds, when used in combination, possess surprising MOC properties, particularly when used to counteract body malodour.

This finding enables these compounds to be used in combination in MOC compositions and products, in particular deodorant and antiperspirant compositions and products, which in turn may be used in a method of counteracting malodour, in particular in a method of counteracting body malodour such as axillary malodour.

The term MOC as used herein refers to the ability of a compound or composition to eliminate or reduce the perception of a malodour.

In a first aspect of the present invention there is provided a MOC composition, in particular a deodorant composition, comprising at least 25% w/w in total of at least 3 compounds drawn from Group A and Group B following:
- A. at least 5% in total of at least one of the following compounds: 2-Cyclohexylidene-2-phenylacetonitrile, 2-Acetyl-1,2,3,4,5,6,7,8-octahydro-1,2,8,8-tetramethylnapthalene, cyclohexylidene(2-methylphenyl)acetonitrile, 2-Ethoxy-4-formylphenyl (E)-3-(2-hydroxyphenyl)acrylate and (E)-Dec-9-enyl 3-(2-hydroxyphenyl)acrylate, 2-Acetyl-1,2,3,4,5,6,7,8-octahydro-1,2,8,8-tetramethylnaphthalene,
- B. optionally, at least one of the following compounds: 3,8,8,11a-Tetramethyldodecahydro-5H-3,5a-epoxy-napth[2,1-C]oxepin, Oxacycloheptadec-10-en-2-one, 3-Methyl-5-(2,2,3-trimethyl-3-cyclopenten-1-yl)-4-penten-2-ol, Ethyl 2,6,6-trimethyl-1,3-cyclohexadiene-1-carboxylate, 2-Methyl-3-(4-methoxyphenyl)propanal, 3-(3-isopropylphenyl)butanal, 2(6)-Methyl-8-(1-methylethyl)bicyclo[2.2.2]oct-5-en-2(3)-yl-1,3-dioxolane, 1-Methyl-2-(1,2,2-trimethylbicyclo[3.1.0]hex-3-ylmethyl)cyclopropyl)methanol, 3,7-Dimethyl-2(3),6-nonadienonitrile, 2-(2-(4-Methyl-3-cyclohexen-1-yl)propyl)cyclopentanone, 2-Cyclohexyl-1,6-heptadien-3-one, (2Z)-2-ethyl-4-(2,2,3-trimethylcyclopent-3-en-1-yl)but-2-en-1-ol, 2-{[1-(3,3-dimethylcyclohexyl)ethyl]oxy}-2-methylpropyl cyclopropanecarboxylate, 1-Spiro[4.5]dec-7-en-7-yl-4-penten-1-one, 1-spiro[4.5]dec-6-en-7-yl-4-penten-1-one, 1-(trimethylcyclododecatrienyl)-Ethanone, 4-cyclooctren-1-yl methyl carbonate, 2-(2,4-dimethylcyclohexyl)-pyridine, wherein the calculation of the weight percentage of every component has been performed on the basis that the presence of any diluent is ignored.

In another aspect of the present invention there is provided a MOC composition, in particular a deodorant composition, comprising at least 25%, or at least 30% w/w in total of at least 5 compounds drawn from Group A and Group B following:
- A. at least 5% in total of at least one of the following compounds: 2-Cyclohexylidene-2-phenylacetonitrile, 2-Acetyl-1,2,3,4,5,6,7,8-octahydro-1,2,8,8-tetramethylnapthalene, cyclohexylidene(2-methylphenyl)acetonitrile, 2-Ethoxy-4-formylphenyl (E)-3-(2-hydroxyphenyl)acrylate and (E)-Dec-9-enyl 3-(2-hydroxyphenyl)acrylate, 2-Acetyl-1,2,3,4,5,6,7,8-octahydro-1,2,8,8-tetramethylnaphthalene,
- B. optionally, at least one of the following compounds: 3,8,8,11a-Tetramethyldodecahydro-5H-3,5a-epoxy-napth[2,1-C]oxepin, Oxacycloheptadec-10-en-2-one, 3-Methyl-5-(2,2,3-trimethyl-3-cyclopenten-1-yl)-4-penten-2-ol, Ethyl 2,6,6-trimethyl-1,3-cyclohexadiene-1-carboxylate, 2-Methyl-3-(4-methoxyphenyl)propanal, 3-(3-isopropylphenyl)butanal, 2(6)-Methyl-8-(1-methylethyl)bicyclo[2.2.2]oct-5-en-2(3)-yl-1,3-dioxolane, 1-Methyl-2-(1,2,2-trimethylbicyclo[3.1.0]hex-3-ylmethyl)cyclopropyl)methanol, 3,7-Dimethyl-2(3),6-nonadienonitrile, 2-(2-(4-Methyl-3-cyclohexen-1-yl)propyl)cyclopentanone, 2-Cyclohexyl-1,6-heptadien-3-one, (2Z)-2-ethyl-4-(2,2,3-trimethylcyclopent-3-en-1-yl)but-2-en-1-ol, 2-{[1-(3,3-dimethylcyclohexyl)ethyl]oxy}-2-methylpropyl cyclopropanecarboxylate, 1-Spiro[4.5]dec-7-en-7-yl-4-penten-1-one, 1-spiro[4.5]dec-6-en-7-yl-4-penten-1-one, 1-(trimethylcyclododecatrienyl)-Ethanone, 4-cyclooctren-1-yl methyl carbonate, 2-(2,4-dimethylcyclohexyl)-pyridine wherein the calculation of the weight percentage of every component has been performed on the basis that the presence of any diluent is ignored.

According to illustrative embodiments the MOC compositions, in particular the deodorant and/or antiperspirant compositions, defined hereinabove comprises at least 10% w/w, or 15% w/w in total of at least 2 compounds selected from group A, as defined hereinabove.

According to illustrative embodiments of the present invention the MOC compositions, in particular the deodorant compositions, defined herein comprises at least 2.5% w/w, 5% w/w, 10% w/w, or 15% w/w of the compound (E)-Dec-9-enyl 3-(2-hydroxyphenyl) acrylate selected from group A, as defined hereinabove.

According to illustrative embodiments of the present invention the MOC compositions, in particular the deodorant compositions, defined hereinabove comprises at least 2.5% w/w, 5% w/w, 10% w/w, or 15% w/w of the compound 2-Cyclohexylidene-2-phenylacetonitrile selected from group A, as defined hereinabove.

According to illustrative embodiments of the present invention the MOC compositions, in particular the deodorant compositions, defined herein comprises at least 5% w/w, 10% w/w, or 15% w/w in total of the compounds 2-Cyclohexylidene-2-phenylacetonitrile and (E)-Dec-9-enyl 3-(2-hydroxyphenyl) acrylate selected from group A, as defined hereinabove.

The group A and B compounds as defined herein may be added into a composition in neat form, or in a solvent, or they may first be modified, for example by entrapped with an entrapment material such as for example polymers, capsules, microcapsules, nanocapsules, liposomes, precursors, film formers, absorbents such as for example by using carbon or zeolites, cyclic oligosaccharides and mixtures thereof, or they may be chemically bound to substrates which are adapted to release the compounds upon application of an exogenous stimulus such as light, enzymes, or the like.

Subject to the constraints detailed herein, the concentrations of group A and B compounds that may be employed in the abovementioned MOC compositions, in particular deodorant compositions, will depend on the particular sensorial effect that the formulator is trying to achieve. These compounds are fragrance compounds and, may influence the overall hedonic or sensorial effect of the composition.

The group A and B compounds as defined herein may be the sole components in a composition. Alternatively they may be employed in conjunction with other compounds commonly used in MOC compositions, more particularly deodorant and/or antiperspirant compositions, e.g. other MOC compounds, other fragrance compounds, excipients, and auxiliary agents.

Other MOC compounds include, but are not limited to, antimicrobial agents, malodour absorbers, chemical neutralisers e.g. acid-base reagents, thiol traps, etc, odour blockers (cf TecnoScent), cross-adaptation agents e.g. as disclosed in U.S. Pat. No. 5,538,719 incorporated herein by reference, malodour complexation agents e.g. various cyclodextrins.

Examples of antimicrobial agents include, but are not limited to, metal salts such as zinc citrate, zinc oxide, zinc pyrethiones, and octopirox; organic acids, such as sorbic acid, benzoic acid, and their salts; parabens, such as methyl paraben, propyl paraben, butyl paraben, ethyl paraben, isopropyl paraben, isobutyl paraben, benzyl paraben, and their salts; alcohols, such as benzyl alcohol, phenyl ethyl alcohol; boric acid; 2,4,4'-trichloro-2-hydroxy-diphenyl ether; phenolic compounds, such as phenol, 2-methyl phenol, 4-ethyl phenol; essential oils such as rosemary, thyme, lavender, eugenol, geranium, tea tree, clove, lemon grass, peppermint, or their active components such as anethole, thymol, eucalyptol, farnesol, menthol, limonene, methyl salicylate, salicylic acid, terpineol, nerolidol, geraniol, and mixtures thereof.

Examples of malodour absorbers include, but are not limited to molecular sieves, such as zeolites, silicas, aluminosilcates, and cyclodextrins; and organic absorbents, such as for example, activated charcoal, dried citrus pulp, cherry pit extract, corncob, and mixtures thereof.

Other fragrance compounds include, but are not limited to, natural products such as extracts, essential oils, absolutes, resinoids, resins, concretes etc., and also synthetic basic substances such as hydrocarbons, alcohols, aldehydes, ketones, ethers, acids, esters, acetals, ketals, nitriles, etc., including saturated and unsaturated compounds, aliphatic, carbocyclic and heterocyclic compounds.

Excipients and auxiliary agents used in MOC compositions are well known in the art and include, without limitation, diluents such as solvents (including water, alcohol, ethanol, oils, fats, vegetable oil, and miglyol, C2-C6 polyhydric alcohols, propylene carbonate, liquid polyalkylene glycols, triethyl citrate, isopropyl myristate, benzyl benzoate, diethyl phthalate, dipropylene glycol (DPG)), binders, disintegranting agents, lubricants, coloring agents, preservatives, antioxidants, emulsifiers, stabilisers, anti-caking agents, and the like.

Further examples of other fragrance compounds, excipients and other auxiliary agents commonly used in conjunction with fragrance and MOC compositions can be found in S. Arctander, Perfume and Flavor Chemicals (Montclair, N.J., 1969); S. Arctander, Perfume and Flavor Materials of Natural Origin (Elizabeth, N.J., 1960); "Flavor and Fragrance Materials—1991", Allured Publishing Co. Wheaton, Ill. USA; S. Arctander, '*Perfume and Flavour Chemicals*', Vol. I and II, Allured Publishing Corporation, Carol Stream, 1994, and J. M. Nikitakis (Ed.), '*CTFA Cosmetic Ingredient Handbook*', 1st ed., The Cosmetic, Toiletry and Fragrance Association, Inc., Washington, 1988.

The MOC compositions, in particular deodorant and/or antiperspirant compositions, disclosed herein may be MOC products in their own right. However, more typically, they would be added to a further composition, possibly comprising further MOC and fragrance ingredients, to form a MOC product, in particular a deodorant and/or antiperspirant product.

Accordingly, in a further illustrative aspect of the present invention there is provided a method of creating or modifying a MOC product, in particularly a deodorant and/or antiperspirant product, comprising the step of adding to said product a composition as defined hereinabove.

The MOC compositions, in particularly the deodorant compositions, as defined herein may be added to a MOC product by using conventional techniques to directly admix said composition into the MOC product, in particular deodorant and/or antiperspirant products.

The amount of an MOC composition, in particularly a deodorant composition, as defined herein, that may be employed in the MOC products, in particular deodorant and/or antiperspirant products, will depend on the purpose and particular sensorial effect that the formulator is trying to achieve. Having regard to these considerations, and the teaching herein, the skilled person will be able, by routine experimentation, to find the appropriate concentration.

In an illustrative embodiment the amount of the MOC composition, in particular deodorant composition as defined herein, that may be added to a MOC product, in particular a deodorant and/or antiperspirant product, is within a range of 0.01% to 40%, 0.01% to 2%, or 0.5% to 2% by weight of the total MOC product composition.

These proportions are meant to be in no way limiting, and it is possible and permissible for the skilled person to work outside these limits, in order to achieve particular effects.

The terms MOC product as used herein refers to all manner of MOC products, non limiting examples of products include talcum powder, deodorants and antiperspirants, lotions, and oils, soap, syndet, soap and syndet personal wash bars, personal wash liquids, and personal wipes, diapers, pantiliners and sanitary products, shampoos, conditioners, styling sprays, mousses, gels, hair wipes, hair sprays, and hair pomades, fabric washing liquids and powders, fabric conditioners, wipes, dishwashing liquids and powders, hard surface cleaning liquids and powders, aqueous and non-aqueous sprays, candles, gels, plug-in electrical devices and battery-operated devices for introducing compositions into spaces, and liquid wicking systems.

In particular the MOC products are deodorant and/or antiperspirant compositions used in personal care products such as deodorants, antiperspirants, talcum powder, soaps, personal wash liquids, and personal wipes.

In an illustrative embodiment of the present invention the MOC product is an antiperspirant or deodorant, particularly an axillary malodour counteracting deodorant or antiperspirant product.

The effectiveness of compositions of the present invention comprising 2-Ethoxy-4-formylphenyl (E)-3-(2-hydroxyphenyl) acrylate and/or (E)-Dec-9-enyl 3-(2-hydroxyphenyl) acrylate, two group A materials, in axillary malodour counteracting deodorant is particularly surprising. These materials are pro perfumes that undergo scission into other compounds when exposed to UV light, this is disclosed in EP 936211. The use of materials that require light activation is counter-intuitive for application in underarm products such as deodorants and antiperspirants. 2-Ethoxy-4-formylphenyl (E)-3-(2-hydroxyphenyl)acrylate and (E)-Dec-9-enyl 3-(2-hydroxyphenyl)acrylate have been found to deliver better deodorancy than their breakdown products.

The MOC compositions and products of the present invention, defined herein, may be applied to a surface to counteract a malodour.

The term "surface" as used herein, refers to any type of surface and includes fabrics, hard surfaces such as wood and plastic, skin, hair, or any combination thereof.

In an illustrative aspect of the present invention there is provided a method of counteracting malodour, the method comprising the application to a surface of a composition or product as defined herein.

In an illustrative embodiment of the present invention the composition or product is a deodorant and/or antiperspirant composition or product and the surface is skin, in particular human skin.

In another illustrative embodiment of the present invention the surface is underarm skin and the malodour is axillary malodour.

The invention will now be described in further detail by way of the following examples.

Example 1

Compositions according to the invention were made and tested for MOC properties in underarm products, using an Odour Reduction Value test generally as described in U.S. Pat. No. 4,278,658. The test was carried out using ca. 50 Caucasian male subjects treated with alcoholic deodorant comprising ca. 1% w/w of the composition under investigation; each panellist was sprayed for 2 seconds in the axillae.

The malodour intensity scale employed by the assessors ran from 0 to 5, with 5 as the highest level of malodour and 0 as no malodour, the intensity being anchored to standard solutions containing specific concentrations of the malodorous acid, isovaleric acid (see Table 1).

TABLE 1

| Standard malodour intensities | | |
|---|---|---|
| Score | Odour Level | Concentrations of aqueous solution of isovaleric acid (ml/l) |
| 0 | No odour | 0 |
| 1 | Slight | 0.013 |
| 2 | Definite | 0.053 |
| 3 | Moderate | 0.22 |
| 4 | Strong | 0.87 |
| 5 | Very strong | 3.57 |

Each composition sampled received a malodour intensity or deo-test score (DST) of between 0 and 5. The DTS was then used in the following formula to calculate the Malodour Inhibition Value (MIV) for the composition.

MIV=(DTSc−DTS)/DTSc (wherein DTSc is the mean malodour score exhibited by a control not containing any fragrance compounds).

The compositions and observed MOC properties (as determined in the Odour Reduction Test) of various mixtures are shown in Table 2(a), (b) and (c). In all cases the sample named M00 represents a control comprising only the solvent dipropylene glycol.

Tables 2(a) and (b) detail compositions according to the present invention. Table 2(c) details compositions not meeting the requirements of the present invention.

| Key to tables 2(a), (b) and (c) | |
|---|---|
| DPG: | Dipropylene glycol |
| S: | Solvent |
| MIV | Mean Inhibition Value |
| *: | Mean of 8 experiments |

TABLE 2A

Compositions and Deodorant Efficacies of Compositions of the Invention

| Compound | Group membership A & B | A | M00 | M61 | M41 | M60 | M23 | M14 |
|---|---|---|---|---|---|---|---|---|
| Oxacycloheptadec-10-en-2-one (Ambrettolide) | Y | 0 | 0 | 0 | 0 | 2 | 0 | 0 |
| 3-methyl-5-cyclotetradecenone (Cosmone) | | 0 | 0 | 0 | 0 | 1 | 0 | 0 | 0 |
| 3-Methyl-5-(2,2,3-trimethyl-3-cyclopenten-1-yl)-4-penten-2-ol (Ebanol) | Y | 0 | 0 | 0 | 0 | 0 | 1 | 0 | 0 |
| Ethyl 2,6,6-trimethyl-1,3-cyclohexadiene-1-carboxylate one (Ethyl safranate) | Y | 0 | 0 | 0 | 0 | 0 | 0 | 1 | 0 |

TABLE 2A-continued

Compositions and Deodorant Efficacies of Compositions of the Invention

| Compound | | | | | | | | |
|---|---|---|---|---|---|---|---|---|
| 2-Methyl-3-(4-methoxyphenyl)propanal one (Fennaldehyde) | Y | 0 | 0 | 0 | 0 | 0 | 0 | 4 |
| 3-(4-ethylphenyl)-2,2-dimethylpropanenitrile (Fleuranil) | 0 | 0 | 0 | 0 | 8 | 0 | 0 | 0 |
| 3-(3-isopropylphenyl)butanal one (Florhydral) | Y | 0 | 0 | 0 | 0 | 4 | 0 | 0 |
| 1-(3,3-dimethylcyclohex-1-en-1-yl)pent-4-en-1-one (Galbanone) | 0 | 0 | 0 | 0 | 0 | 0 | 0.1 | 0 |
| 2-acetyl-1,2,3,4,5,6,7,8-octahydro-1,2,8,8-tetramethylnaphthalene (Georgywood) | Y | Y | 0 | 8 | 8 | 8 | 8 | 8 |
| Ethyl 2-ethyl-6,6-dimethylcyclohex-2-ene-1-carboxylate (Givescone) | 0 | 0 | 0 | 0 | 0 | 0 | 1 | 0 |
| 2(6)-Methyl-8-(1-methylethyl) bicyclo[2.2.2] oct-5-en-2(3)-yl-1,3-dioxolane one (Glycolierral) | Y | 0 | 0 | 1 | 0 | 0 | 0 | 0 |
| 1-methyl-2-{[(1,2,2-trimethylbicyclo[3.1.0]hex-3-yl]methyl}cyclopropyl)methanol (Javanol) | Y | 0 | 0 | 0 | 0 | 0 | 0 | 1 |
| 2,5,5-trimethyl-6,6-bis(methyloxy)hex-2-ene (Methyl pamplemousse) | 0 | 0 | 0 | 1 | 0 | 0 | 0 | 1 |
| 1,4-dioxacyclohexadecane-5,16-dione (Musk MC4) | 0 | 0 | 0 | 0 | 0 | 0 | 0 | 8 |
| 2,4-dimethyl-2-(5,5,8,8-tetramethyl-5,6,7,8-tetrahydronaphthalen-2-yl)-1,3-dioxolane (Okoumal) | 0 | 0 | 0 | 1 | 0 | 0 | 1 | 0 |
| 2-Cyclohexylidene-2-phenylacetonitrile (Peonile) | Y | Y | 0 | 0 | 8 | 0 | 0 | 0 |
| Pharaone | Y | 0 | 0 | 0 | 0 | 0 | 0.1 | 0 |
| 2-{[1-(3,3-dimethylcyclohexyl)ethyl]oxy}-2-methylpropyl cyclopropanecarboxylate (Serenolide) | Y | 0 | 0 | 0 | 0 | 0 | 0 | 8 |
| Silvanone ™ | 0 | 0 | 0 | 0 | 0 | 16 | 0 | 0 |
| 5-methylheptan-3-one oxime (Stemone) | 0 | 0 | 0 | 0 | 1 | 0 | 0 | 0 |
| (E)-Dec-9-enyl 3-(2-hydroxyphenyl) acrylate (Tonkarose) | Y | Y | 0 | 1.6 | 0 | 0 | 0 | 0 |
| 1-cyclopropylmethyl-4-methoxy-benzene (Toscanol) | 0 | 0 | 0 | 0 | 0 | 1 | 0 | 0 |
| Cyclohexadec-5-enone (Velvione) | 0 | 0 | 0 | 2 | 0 | 0 | 0 | 0 |
| 4-cycloocten-1-yl methyl (Violiff) | Y | 0 | 0 | 1 | 0 | 0 | 0 | 0 |
| DPG | S | S | 100 | 85.4 | 73 | 68 | 88.8 | 70 |
| total % | | | 100 | 100 | 100 | 100 | 100 | 100 |
| Group Analysis: | | | M00 | M61 | M41 | M60 | M23 | M14 |
| % of fragrance compounds in total composition (inc. diluent) | | | 0 | 14.6 | 27 | 32 | 10.2 | 30 |
| No. of Group A & B compounds | | | 0 | 3 | 3 | 4 | 3 | 4 |
| % of Group A & B compounds in total composition (inc. diluent) | | | 0 | 10.6 | 17 | 15 | 9.1 | 21 |

TABLE 2A-continued

Compositions and Deodorant Efficacies of Compositions of the Invention

| | | | | | | |
|---|---|---|---|---|---|---|
| Fragrance component % of Group A & B compounds (diluent ignored) | 0 | 72.60 | 62.96 | 46.88 | 81.25 | 70.00 |
| No. of Group A compounds | 0 | 2 | 2 | 1 | 1 | 1 |
| % of Group A compounds in total composition (inc. diluent) | 0 | 9.6 | 16 | 8 | 8 | 8 |
| Fragrance component % of group A compounds (diluent ignored) | 0 | 65.75 | 59.26 | 25 | 78.43 | 26.67 |
| Deo Efficacy: | | | | | | |
| deo-test score DTS | 2.01* | 1.00 | 1.08 | 1.10 | 1.22 | 1.27 |
| MIV (DPG = 2.01) | 0 | 0.50 | 0.46 | 0.45 | 0.39 | 0.37 |

TABLE 2(b)

Compositions and Deodorant Efficacies of Compositions of the Invention

| Compound | Group membership A & B | A | M00 | M7 | M43 | M57 | M38 | M9 |
|---|---|---|---|---|---|---|---|---|
| 3,8,8,11a-Tetramethyldodecahydro-5H-3,5a-epoxy-napth [2,1-C] oxepin (Amberketal) | Y | 0 | 0 | 0.1 | 0.1 | 0 | 0.1 | 0 |
| 3-methyl-5-cyclotetradecenone (Cosmone) | 0 | 0 | 0 | 0 | 0 | 1 | 0 | 0 |
| 2,6-dimethyloct-7-en-2-ol | 0 | 0 | 0 | 0 | 0 | 0 | 16 | 0 |
| Ethyl 2,6,6-trimethyl-1,3-cyclohexadiene-1-carboxylate one (Ethyl safranate) | Y | 0 | 0 | 0 | 0 | 0 | 0 | 1 |
| 2-Methyl-3-(4-methoxyphenyl)propanal one (Fennaldehyde) | Y | 0 | 0 | 0 | 4 | 0 | 0 | 0 |
| 2-(1-methylpropyl)cyclohexanone (Freskomenthe) | 0 | 0 | 0 | 0 | 0 | 0 | 1 | 0 |
| 1-(3,3-dimethylcyclohex-1-en-1-yl)pent-4-en-1-one (Galbanone) | 0 | 0 | 0 | 0.1 | 0 | 0 | 0 | 0 |
| 2-acetyl-1,2,3,4,5,6,7,8-octahydro-1,2,8,8-tetramethylnaphthalene (Georgywood) | Y | Y | 0 | 0 | 0 | 0 | 8 | 0 |
| 2-{[1-(3,3-dimethylcyclohexyl)ethyl]oxy}-2-methylpropyl propanoate (Helvetolide) | 0 | 0 | 0 | 0 | 0 | 0 | 0 | 4 |
| 2,4,4,7-tetramethylnona-6,8-dien-3-one oxime (Labienoxime) | 0 | 0 | 0 | 0.01 | 0 | 0 | 0 | 0 |
| 3,7-dimethylnona-2,6-dienenitrile (Lemonile) | Y | 0 | 0 | 0 | 0 | 0 | 4 | 0 |
| 2,5,5-trimethyl-6,6-bis(methyloxy)hex-2-ene (Methyl pamplemousse) | 0 | 0 | 0 | 1 | 0 | 0 | 0 | 0 |
| 2-[2-(4-methylcyclohex-3-en-1-yl)propyl]cyclopentanone (Nectaryl) | Y | 0 | 0 | 0 | 2 | 0 | 0 | 0 |
| 2-ethyl-n-methyl-n-(3-methylphenyl)butanamide (Paradisamide) | 0 | 0 | 0 | 0 | 0 | 2 | 0 | 0 |
| 2-Cyclohexylidene-2-phenylacetonitrile (Peonile) | Y | Y | 0 | 8 | 0 | 0 | 0 | 0 |
| 5,6,7-trimethylocta-2,5-dien-4-one (Pomarose) | 0 | 0 | 0 | 0 | 0 | 0 | 0 | 1 |
| 2-ethyl-4-(2,2,3-trimethylcyclopent-3-en-1-yl)but-2-en-1-ol (Radjanol Super) | Y | 0 | 0 | 0 | 0 | 4 | 0 | 0 |

TABLE 2(b)-continued

Compositions and Deodorant Efficacies of Compositions of the Invention

| Compound | | | | | | | | |
|---|---|---|---|---|---|---|---|---|
| 1-methyl-3-(2-methylpropyl)cyclohexanol (Rossitol) | 0 | 0 | 0 | 0 | 0 | 0 | 8 | 0 |
| 2-{[1-(3,3-dimethylcyclohexyl)ethyl]oxy}-2-methylpropyl cyclopropanecarboxylate (Serenolide) | Y | 0 | 0 | 0 | 0 | 8 | 0 | 0 |
| Silvanone ™ | 0 | 0 | 0 | 0 | 16 | 0 | 0 | 0 |
| 1-Spiro[4.5]dec-7-en-7-yl-4-penten-1-one & 1-spiro[4.5]dec-6-en-7-yl-4-penten-1-one (Spirogalbanone) | Y | 0 | 0 | 0 | 0 | 0 | 0 | 0.1 |
| 5-methylheptan-3-one oxime (Stemone) | 0 | 0 | 0 | 0 | 0 | 0 | 0 | 1 |
| 6-ethyl-3-methyl-6-octenol (Super Muguet) | 0 | 0 | 0 | 0 | 4 | 4 | 0 | 0 |
| (E)-Dec-9-enyl 3-(2-hydroxyphenyl) acrylate (Tonkarose) | Y | Y | 0 | 0 | 1.6 | 1.6 | 0 | 1.6 |
| 1-(trimethylcyclododecatrienyl)-Ethanone (Trimofix O) | Y | 0 | 0 | 1 | 0 | 0 | 0 | 0 |
| DPG | S | S | 100 | 89.79 | 72.3 | 79.4 | 62.9 | 91.3 |
| total % | | | | 100 | 100 | 100 | 100 | 100 |
| Group Analysis: | | | M00 | M7 | M43 | M57 | M38 | M9 |
| % of fragrance compounds in total composition (inc. diluent) | | | 0 | 10.21 | 27.7 | 20.6 | 37.1 | 8.7 |
| No. of Group A & B compounds | | | 0 | 3 | 3 | 3 | 3 | 3 |
| % of Group A & B compounds in total composition (inc. diluent) | | | 0 | 9.1 | 7.7 | 13.6 | 12.1 | 2.7 |
| Fragrance component % of Group A & B compounds (diluent ignored) | | | 0 | 89.13 | 27.80 | 66.02 | 32.61 | 31.03 |
| No. of Group A compounds | | | 0 | 1 | 1 | 1 | 1 | 1 |
| % of Group A compounds in total composition (inc. diluent) | | | 0 | 8 | 1.6 | 1.6 | 8 | 1.6 |
| Fragrance component % of group A compounds (diluent ignored) | | | 0 | 78.35 | 5.78 | 7.77 | 22.16 | 18.39 |
| Deo Efficacy: | | | | | | | | |
| Score DTS | | | 2.01* | 1.29 | 1.33 | 1.40 | 1.43 | 1.46 |
| MIV (DPG = 2.01) | | | 0 | 0.36 | 0.34 | 0.30 | 0.29 | 0.27 |

TABLE 2(c)

Compositions and Deodorant Efficacies of Compositions of the Invention

| Compounds | Group membership A & B | A | M00 | SAMPLES (comparatives) C27 | C44 | C48 | C11 | C16 |
|---|---|---|---|---|---|---|---|---|
| Octahydro-2H-chromen-2-one (Bicyclononalactone) | 0 | 0 | 0 | 0 | 1 | 0 | 0 | 0 |
| Dihydro beta ionone | 0 | 0 | 0 | 0 | 0 | 4 | 0 | 0 |
| 2,6-dimethyloct-7-en-2-ol | 0 | 0 | 0 | 16 | 0 | 16 | 16 | 0 |
| (4E)-3-methyl-5-(2,2,3-trimethylcyclopent-3-en-1-yl)pent-4-en-2-ol (Ebanol) | Y | 0 | 0 | 0 | 1 | 0 | 0 | 0 |
| 3-(3-isopropylphenyl)butanal one (Florhydral) | Y | 0 | 0 | 0 | 0 | 0 | 4 | 0 |
| 1-[(3Z)-cyclooct-3-en-1-yl]propan-1-ol (Florymoss) | 0 | 0 | 0 | 0 | 1 | 0 | 0 | 0 |

TABLE 2(c)-continued

Compositions and Deodorant Efficacies of Compositions of the Invention

| | | | | | | | | |
|---|---|---|---|---|---|---|---|---|
| 2-(1-methylpropyl)cyclohexanone (Freskomenthe) | 0 | 0 | 0 | 0 | 1 | 0 | 0 | 1 |
| 1-(3,3-dimethylcyclohex-1-en-1-yl)pent-4-en-1-one (Galbanone) | 0 | 0 | 0 | 0 | 0.1 | 0 | 0 | 0 |
| Ethyl 2-ethyl-6,6-dimethylcyclohex-2-ene-1-carboxylate (Givescone) | 0 | 0 | 0 | 0 | 0 | 1 | 1 | 0 |
| 2-{[1-(3,3-dimethylcyclohexyl)ethyl]oxy}-2-methylpropyl propanoate (Helvetolide) | 0 | 0 | 0 | 0 | 0 | 0 | 0 | 4 |
| 1-methyl-2-{[(1,2,2-trimethylbicyclo[3.1.0]hex-3-yl]methyl}cyclopropyl)methanol (Javanol) | Y | 0 | 0 | 1 | 0 | 0 | 0 | 0 |
| 2,4,4,7-tetramethylnona-6,8-dien-3-one oxime (Labienoxime) | 0 | 0 | 0 | 0.01 | 0 | 0 | 0.01 | 0 |
| 1,4-dioxacyclohexadecane-5,16-dione (Musk MC4) | 0 | 0 | 0 | 0 | 0 | 0 | 0 | 8 |
| 2-Cyclohexylidene-2-phenylacetonitrile (Peonile) | Y | Y | 0 | 0 | 0 | 0 | 0 | 8 |
| 2-ethyl-4-(2,2,3-trimethylcyclopent-3-en-1-yl)but-2-en-1-ol (Radjanol Super) | Y | 0 | 0 | 0 | 0 | 0 | 4 | 4 |
| Silvanone ™ | 0 | 0 | 0 | 16 | 0 | 0 | 0 | 0 |
| 5-methylheptan-3-one oxime (Stemone) | 0 | 0 | 0 | 0 | 0 | 0 | 1 | 0 |
| (E)-Dec-9-enyl 3-(2-hydroxyphenyl) acrylate (Tonkarose) | Y | Y | 0 | 1.6 | 1.6 | 1.6 | 0 | 0 |
| 1-cyclopropylmethyl-4-methoxy-benzene (Toscanol) | 0 | 0 | 0 | 0 | 0 | 1 | 0 | 1 |
| undeca-1,3,5-triene (Undecatriene) | 0 | 0 | 0 | 0 | 0 | 1 | 0 | 0 |
| 2-(2,4-dimethylcyclohexyl)-pyridine (Zinarine) | Y | 0 | 0 | 2 | 0 | 0 | 0 | 0 |
| DPG | S | S | 100 | 63.39 | 94.3 | 75.4 | 73.99 | 74 |
| | | | | | | | | |
| total % | | | 100 | 100 | 100 | 100 | 100 | 100 |
| | | | | | | | | |
| Group Analysis | | | M00 | C27 | C44 | C48 | C11 | C16 |
| | | | | | | | | |
| % of fragrance compounds in total composition (inc. diluent) | | | 0 | 36.61 | 5.7 | 24.6 | 26.01 | 26 |
| No. of Group A & B compounds | | | 0 | 3 | 2 | 1 | 2 | 2 |
| % of Group A & B compounds in total composition (inc. diluent) | | | 0 | 4.6 | 2.6 | 1.6 | 8 | 12 |
| Fragrance component % of Group A & B compounds (diluent ignored) | | | 0 | 12.56 | 45.61 | 6.50 | 30.76 | 46.15 |
| No. of Group A compounds | | | 0 | 1 | 1 | 1 | 0 | 1 |
| % of Group A compounds in total composition (inc. diluent) | | | 0 | 1.6 | 1.6 | 1.6 | 0 | 8 |
| Fragrance component % of group A compounds (diluent ignored) | | | 0 | 4.37 | 28.07 | 6.50 | 0 | 30.77 |
| Deo Efficacy | | | | | | | | |
| | | | | | | | | |
| Score DTS | | | 2.01* | 1.64 | 1.68 | 1.76 | 1.81 | 1.87 |
| MIV (DPG = 2.01) | | | 0 | 0.18 | 0.16 | 0.12 | 0.07 | 0.07 |

The compositions according to the present invention detailed in Tables 2(a) and (b) exhibit good deodorancy (e.g. MIV>0.25 in the Odour Reduction Value Test) whereas the compositions not meeting the requirements of the present invention detailed in of Table 2(c) display poor deodorant performance.

Compositions containing around 10% of two Group A compounds show particularly good deodorancy (MIV>0.4).

Example 2

Table 3 details example compositions according to the present invention that are more complex than earlier examples, and more suitable for meeting the hedonic needs of products such as deodorant and antiperspirant products.

TABLE 3

| Compound | Group Membership A | Group Membership B | SAMPLES (comparatives) % (w/w) CPD/1/09 | CPD/2/09 | CPD/3/09 |
|---|---|---|---|---|---|
| 2-Phenylethanol | 0 | 0 | 30 | 10 | 7.5 |
| Oxacycloheptadec-10-en-2-one (Ambrettolide) | 0 | 1 | | | 0.5 |
| Benzyl acetate | 0 | 0 | | | 5 |
| DPG | S | S | 30 | 32.4 | 41.56 |
| 3-Methyl-5-(2,2,3-trimethyl-3-cyclopenten-1-yl)-4-penten-2-ol (Major component of Ebanol) | 0 | 1 | 3 | | |
| Ethyl 2,6,6-trimethyl-1,3-cyclohexadiene-1-carboxylate one (Ethyl safranate) | 0 | 1 | 0.5 | | |
| 2-Methyl-3-(4-methoxyphenyl)propanal one (Fennaldehyde) | 0 | 1 | | | 2 |
| 3-(3-isopropylphenyl)butanal one (Florhydral) | 0 | 1 | | | 4 |
| 2-acetyl-1,2,3,4,5,6,7,8-octahydro-1,2,8,8-tetramethylnaphthalene (Georgywood) | 1 | 0 | 2 | 2 | |
| Geranyl acetate | 0 | 0 | | 5 | 5 |
| Hexyl cinnamic aldehyde | 0 | 0 | 7 | 5 | 6 |
| 3-pentyltetrahydro-2H-pyran-4-yl acetate (Jasmopyrane Forte) | 0 | 0 | | | 1 |
| 3,7-dimethylnona-2,6-dienenitrile (Lemonile) | 0 | 1 | 2 | 5 | |
| Linalol | 0 | 0 | 6.3 | 12 | |
| 2-[2-(4-methylcyclohex-3-en-1-yl)propyl]cyclopentanone (Nectaryl) | 0 | 1 | 1 | | |
| Nerol | 0 | 0 | 3 | 5 | |
| Orange Terpenes | 0 | 0 | | 9 | 10 |
| 2-Cyclohexylidene-2-phenylacetonitrile (Peonile) | 1 | 0 | 3 | 9 | 12 |
| 2-Cyclohexylhepta-1,6-dien-3-one (Pharaone) 10% in diluent | 0 | 1 | 0.2 | | |
| 2-ethyl-4-(2,2,3-trimethylcyclopent-3-en-1-yl)but-2-en-1-ol (Radjanol Super) | 0 | 1 | 1 | | 4 |
| 2-{[1-(3,3-dimethylcyclohexyl)ethyl]oxy}-2-methylpropyl cyclopropanecarboxylate (Serenolide) | 0 | 1 | 10 | 4 | |
| 1-Spiro[4.5]dec-7-en-7-yl-4-penten-1-one and 1-spiro[4.5]dec-6-en-7-yl-4-penten-1-one (Both components of Spirogalbanone) Spirogalbanone 10% in diluent | 0 | 1 | | | 0.2 |
| (E)-Dec-9-enyl 3-(2-hydroxyphenyl) acrylate (Tonkarose) | 1 | 0 | | 1.6 | 1.04 |
| Undecalactone | 0 | 0 | 1 | | |
| 2-(2,4-dimethylcyclohexyl)-pyridine (Zinarine) | 0 | 1 | | | 0.2 |
| Total % | | | 100 | 100 | 100 |

TABLE 3-continued

| Compound | Group Membership | | SAMPLES (comparatives) % (w/w) | | |
|---|---|---|---|---|---|
| | A | B | CPD/1/09 | CPD/2/09 | CPD/3/09 |
| Solvent total % | | | 30.18 | 32.4 | 41.74 |
| No. of Group A Compounds | | | 2 | 3 | 2 |
| Sum of Group A Compounds % | | | 5 | 12.6 | 13.04 |
| No. of Group B Compounds | | | 7 | 2 | 6 |
| Sum of Group B Compounds % | | | 17.52. | 9 | 10.72. |
| Sum of Groups A & B | | | 22.52. | 21.6 | 23.76 |
| Sum of Groups A & B (solv adj) % | | | 32.25 | 31.95 | 40.78 |

The invention claimed is:

1. A MOC composition, comprising at least 25% w/w in total of at least 3 compounds drawn from Group A and optionally from Group B:
   Group A: at least 5% in total of at least one of the following compounds: 2-cyclohexylidene-2-phenylacetonitrile, 2-acetyl-1,2,3,4,5,6,7,8-octahydro-1,2,8,8-tetramethyl-napthalene, cyclohexylidene(2-methylphenyl)acetonitrile, 2-ethoxy-4-formylphenyl (E)-3-(2-hydroxyphenyl)acrylate, (E)-dec-9-enyl 3-(2-hydroxyphenyl)acrylate, 2-acetyl-1,2,3,4,5,6,7,8-octahydro-1,2,8,8-tetramethylnaphthalene,
   Group B: at least one of the following compounds: 3,8,8,11-tetramethyldodecahydro-5H-3,5-epoxy-napth[2,1]oxepin, oxacycloheptadec-10-en-2-one, 3-methyl-5-(2,2,3-trimethyl-3-cyclopenten-1-yl)-4-penten-2-ol, ethyl-2,6,6-trimethyl-1,3-cyclohexadiene-1-carboxylate, 2-methyl-3-(4-methoxyphenyl)propanal, 3-(3-isopropylphenyl)butanal, 2-(6)-methyl-8-(1-methylethyl)bicyclo[2.2.2]oct-5-en-2(3)-yl-1,3-dioxolane, 1-methyl-2-(1,2,2-trimethylbicyclo[3.1.0]-hex-3-ylmethyl)cyclopropyl)methanol, 3,7-dimethyl-2(3),6-nonadienonitrile, 2-(2-(4-methyl-3-cyclohexen-1-yl)propyl)cyclopentanone, 2-cyclohexyl-1,6-heptadien-3-one, (2Z)-2-ethyl-4-(2,2,3-trimethylcyclopent-3-en-1-yl)but-2-en-1-ol, 2-{[1-(3,3-dimethylcyclohexyl)ethyl]oxy}-2-methylpropyl cyclopropanecarboxylate, 1-spiro[4.5]dec-7-en-7-yl-4-penten-1-one, 1-spiro[4.5]dec-6-en-7-yl-4-penten-1-one, 1-(trimethylcyclododecatrienyl)-ethanone, 4-cycloocten-1-yl methyl carbonate, 2-(2,4-dimethylcyclohexyl)-pyridine,
   wherein the calculation of the weight percentage of every component is performed on the basis that the presence of any diluent is ignored in the calculation.

2. A MOC composition according to claim 1 comprising at least 25% w/w in total of at least 5 compounds drawn from Group A and optionally from Group B:
   Group A: at least 5% in total of at least one of the following compounds: 2-cyclohexylidene-2-phenylacetonitrile, 2-acetyl-1,2,3,4,5,6,7,8-octahydro-1,2,8,8-tetramethyl-napthalene, cyclohexylidene(2-methylphenyl)acetonitrile, 2-ethoxy-4-formylphenyl(E)-3-(2-hydroxyphenyl)acrylate, (E)-dec-9-enyl 3-(2-hydroxyphenyl)acrylate, 2-acetyl-1,2,3,4,5,6,7,8-octahydr-1,2,8,8-tetramethylnaphthalene,
   Group B: at least one of the following compounds: 3,8,8,11-tetramethyldodecahydro-5H-3,5-epoxy-napth[2,1]oxepin, oxacycloheptadec-10-en-2-one, 3-methyl-5-(2,2,3-trimethyl-3-cyclopenten-1-yl)-4-penten-2-ol, ethyl 2,6,6-trimethyl-1,3-cyclohexadiene-1-carboxylate, 2-methyl-3-(4-methoxyphenyl)propanal, 3-(3-isopropylphenyl)butanal, 2(6)-methyl-8-(1-methylethyl)bicyclo[2.2.2]oct-5-en-2(3)-yl-1,3-dioxolane, 1-methyl-2-(1,2,2-trimethylbicyclo[3.1.0]-hex-3-ylmethyl)cyclopropyl)methanol, 3,7-dimethyl-2(3),6-nonadienonitrile, 2-(2-(4-methyl-3-cyclohexen-1-yl)propyl)cyclopentanone, 2-cyclohexyl-1,6-heptadien-3-one, (2Z)-2-ethyl-4-(2,2,3-trimethylcyclopent-3-en-1-yl)but-2-en-1-ol, 2-{[1-(3,3-dimethylcyclohexyl)ethyl]oxy}-2-methylpropyl cyclopropanecarboxylate, 1-spiro[4.5]dec-7-en-7-yl-4-penten-1-one, 1-spiro[4.5]dec-6-en-7-yl-4-penten-1-one, 1-(trimethylcyclododecatrienyl)-ethanone, 4-cycloocten-1-yl methyl carbonate, 2-(2,4-dimethylcyclohexyl)-pyridine
   wherein the calculation of the weight percentage of every component is performed on the basis that the presence of any diluent is ignored in the calculation.

3. A MOC composition of claim 2 comprising at least 30% of at least 5 compounds selected from Group A and B.

4. A MOC composition according to claim 1 comprising at least 10% of at least 2 compounds selected from Group A.

5. A MOC composition according to claim 1 comprising at least 2.5% of (E)-dec-9-enyl 3-(2-hydroxyphenyl)acrylate selected from Group A.

6. A MOC composition according to claim 1 comprising at least 5% of 2-cyclohexylidene-2-phenylacetonitrile selected from Group A.

7. A MOC composition according to claim 1 comprising at least 10% w/w of the compounds 2-cyclohexylidene-2-phenylacetonitrile and (E)-dec-9-enyl 3-(2-hydroxyphenyl)acrylate selected from Group A.

8. A method of creating or modifying a MOC product, comprising the step of adding to said product a MOC composition according to claim 1.

9. A MOC product comprising a MOC composition according to claim 1.

10. A MOC product comprising 0.01% to 40% w/w of a MOC composition as defined in claim 1.

11. The MOC product according to claim 9 which is selected from a deodorant or an antiperspirant.

12. A method of counteracting a malodour, the method comprising the application to a surface of a MOC composition according to claim 1.

13. A method of claim 12 wherein the surface is human skin.

* * * * *